(12) United States Patent
Huish et al.

(10) Patent No.: US 7,772,176 B2
(45) Date of Patent: *Aug. 10, 2010

(54) DETERGENT COMPOSITIONS CONTAINING α-SULFOFATTY ACID ESTERS AND METHODS OF MAKING AND USING THE SAME

(75) Inventors: Paul Danton Huish, Salt Lake City, UT (US); Laurie A. Jensen, Midvale, UT (US); Pule B. Libe, Salt Lake City, UT (US)

(73) Assignee: The Sun Products Corporation, Wilton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/780,453

(22) Filed: Jul. 19, 2007

(65) Prior Publication Data

US 2008/0070822 A1    Mar. 20, 2008

Related U.S. Application Data

(63) Continuation of application No. 10/737,102, filed on Dec. 15, 2003, now abandoned, which is a continuation of application No. 09/574,996, filed on May 19, 2000, now Pat. No. 6,683,039.

(51) Int. Cl.
    *C11D 17/00*    (2006.01)
(52) U.S. Cl. .................. 510/357; 510/424; 510/426; 510/428; 510/450; 510/492
(58) Field of Classification Search .............. None
    See application file for complete search history.

(56) References Cited

U.S. PATENT DOCUMENTS

| | | |
|---|---|---|
| 2,043,476 A | 6/1936 | Farbenund |
| 3,962,107 A | 6/1976 | Levin et al. |
| 3,997,576 A | 12/1976 | Oghoshi et al. |
| 4,064,062 A | 12/1977 | Yurko |
| 4,219,435 A | 8/1980 | Biard et al. |
| 4,374,056 A | 2/1983 | Watanabe et al. |
| 4,416,809 A | 11/1983 | Magari et al. |
| 4,438,025 A | 3/1984 | Satsuki et al. |
| 4,476,043 A | 10/1984 | O'Lenick |
| 4,487,710 A | 12/1984 | Kaminsky |
| 4,488,989 A | 12/1984 | Lamberti |
| 4,552,681 A | 11/1985 | Koch et al. |
| 4,597,898 A | 7/1986 | Vander Meer |
| 4,705,644 A | 11/1987 | Barone et al. |
| 4,849,125 A | 7/1989 | Seiter |
| 4,923,628 A | 5/1990 | Appel |
| 4,931,202 A | 6/1990 | Cotter et al. |
| 5,026,400 A | 6/1991 | Holland et al. |
| 5,104,567 A | 4/1992 | Staehr |
| 5,133,892 A | 7/1992 | Chun et al. |
| 5,143,639 A | 9/1992 | Krawack |
| 5,213,705 A | 5/1993 | Olson |
| 5,225,100 A | 7/1993 | Fry et al. |
| 5,324,649 A | 6/1994 | Arnold |
| 5,380,453 A | 1/1995 | Krawack |
| 5,382,677 A | 1/1995 | Colignon et al. |
| 5,387,373 A | 2/1995 | Naik |
| 5,391,783 A | 2/1995 | Colignon et al. |
| 5,397,494 A | 3/1995 | Vega et al. |
| 5,429,773 A | 7/1995 | Sherry et al. |
| 5,475,134 A | 12/1995 | Baker |
| 5,482,644 A | 1/1996 | Nguyen et al. |
| 5,602,089 A | 2/1997 | Pennaz |
| 5,616,781 A * | 4/1997 | Sajic et al. ............. 510/221 |
| 5,624,906 A | 4/1997 | Vermeer |
| 5,637,560 A | 6/1997 | Raehse et al. |
| 5,637,758 A | 6/1997 | Sajic et al. |
| 5,688,982 A | 11/1997 | Khan et al. |
| 5,691,296 A | 11/1997 | Agar |
| 5,783,540 A | 7/1998 | Secemski et al. |
| 5,821,207 A | 10/1998 | Kanai et al. |
| 5,851,976 A | 12/1998 | Mertens |
| 5,900,399 A | 5/1999 | Seiter et al. |
| 5,919,747 A | 7/1999 | Kazuta et al. |
| 5,945,394 A | 8/1999 | Sajic et al. |
| 5,958,864 A | 9/1999 | Gonzalez |
| 5,961,662 A | 10/1999 | Yamaguchi et al. |

(Continued)

FOREIGN PATENT DOCUMENTS

DE    3237001    4/1984

(Continued)

OTHER PUBLICATIONS

"ACUSOL® detergent polymers—ACUSOL® 445 dispersant," *ROHM and HAAS technology report* (1991).

(Continued)

*Primary Examiner*—Necholus Ogden, Jr.
(74) *Attorney, Agent, or Firm*—Sterne, Kessler, Goldstein & Fox P.L.L.C.

(57) ABSTRACT

The present invention includes a composition comprising an enriched mixture of α-sulfofatty acid esters. Increasing the concentration of specific chain length α-sulfofatty acid esters, relative to the proportions of the other chain lengths, allows the detergent compositions to exhibit an improved cleaning performance while simultaneously cleaning a wide variety of materials.

12 Claims, No Drawings

U.S. PATENT DOCUMENTS

| | | | |
|---|---|---|---|
| 5,965,500 | A | 10/1999 | Puvvada |
| 5,965,508 | A | 10/1999 | Ospinal et al. |
| 5,968,891 | A | 10/1999 | Mallari |
| 5,972,861 | A | 10/1999 | Rolfes |
| 5,980,580 | A | 11/1999 | Yamaguchi |
| 6,013,611 | A | 1/2000 | Thomas et al. |
| 6,025,320 | A | 2/2000 | Appel |
| 6,046,151 | A | 4/2000 | Drapier et al. |
| 6,057,280 | A | 5/2000 | Huish et al. |
| 6,060,440 | A | 5/2000 | Sackariasen et al. |
| 6,172,026 | B1 | 1/2001 | Ospinal et al. |
| 6,288,020 | B1 | 9/2001 | Huish et al. |
| 6,303,558 | B1 | 10/2001 | Emery et al. |
| 6,407,050 | B1 | 6/2002 | Huish et al. |
| 6,468,956 | B1 | 10/2002 | Huish et al. |
| 6,509,310 | B1 | 1/2003 | Huish et al. |
| 6,534,464 | B1 | 3/2003 | Huish et al. |
| 6,683,039 | B1 | 1/2004 | Huish et al. |
| 6,764,989 | B1 | 7/2004 | Huish et al. |
| 6,770,611 | B2 | 8/2004 | Huish et al. |
| 6,780,830 | B1 | 8/2004 | Huish et al. |

FOREIGN PATENT DOCUMENTS

| | | |
|---|---|---|
| EP | 0 336 740 B1 | 1/1995 |
| EP | 1 032 640 A | 9/2000 |
| GB | 2 151 656 A | 11/1984 |
| WO | WO 93/12216 | 6/1993 |

OTHER PUBLICATIONS

"ACUSOL® detergent polymers—ACUSOL® 460N dispersant," *ROHM and HAAS technology report*.

"ACUSOL® detergent polymers—ACUSOL® 820 thickener," *ROHM and HAAS technology report*.

Database WPI, Week 9025, Derwent Publications Ltd. (XP002240608).

Davidsohn & Milwidsky, "Synthetic Detergents," *Longman Scientific & Technical*, 7th ed., pp. 263-264 (1987).

Foster, N. and Hovda, K., "Manufacture of Methyl Ester Sulfonates and Other Derivatives," *Chemithon*, Seattle, WA (Oct. 1997).

Foster, N. et al., "Medium to Very High Active Single Step Neutralization," *Chemithon*, Seattle, WA (1997).

Foster, N., "Sulfonation and Sulfation Processes," *Chemithon*, Seattle, WA (1997).

"Fats and Oils Composition" chart, Witco Corporation.

Hovda, K., "Methyl Ester Sulfonation: Process Optimization," *Chemithon*, Seattle, WA (1993).

Hovda, K., "The Challenge of Methylester Sulfonation," *Chemithon*, Seattle, WA (1997).

MacArthur, B. et al., "Meeting the Challenge of Methylester Sulfonation," *Chemithon*, Seattle, WA (1998).

N-octyl pyrrolidone, Internet website: http://www.chemfinder.com (printed Feb. 22, 2000).

Patterson, H.B.W., "Hydrogenation Methods," *Hydrogenation of Fats and Oils*, Elsevier Science Publishing Co., N.Y., pp. 132-231 (1983).

Rao, Y. K. et al., "Physico-Chemical Properties of Some Salts of Sulfo Methyl Ester Surfactants," *4th World Surfactants Congress*, pp. 382-391, (1996).

"Surfactants," *Inform*, 7(1):10-12 (Jan. 1996).

*Technical Bulletin*—"EMPIGEN OB / EBA," Albright & Wilson Americas Inc., Virginia.

\* cited by examiner

DETERGENT COMPOSITIONS CONTAINING α-SULFOFATTY ACID ESTERS AND METHODS OF MAKING AND USING THE SAME

CONTINUING DATA

This application is a continuation of Ser. No. 10/737,102 filed Dec. 15, 2003 now abandoned which is a continuation of Ser. No. 09/574,996, filed May 19, 2000, now U.S. Pat. No. 6,683,039.

BACKGROUND OF THE INVENTION

The present invention generally relates to α-sulfofatty acid ester compositions and methods for making and using such compositions. More particularly, the present invention relates to α-sulfofatty acid ester compositions that are enriched for particular α-sulfofatty acid esters, and methods for making and using such compositions.

Detergents have been used for many years to clean clothing and other materials. Detergent compositions are generally formulated to contain components such as surfactants, builders, electrolytes and other additives dispersed or dissolved in an aqueous medium. Surfactants are included in detergents to enhance their cleaning performance. Typical surfactants include anionics, nonionics, zwitterionics, ampholytics, cationics and those described in *Surface Active Agents*, Volumes I and II by Schwartz, Perry and Berch (New York, Interscience Publishers), *Nonionic Surfactants* ed. by M. J. Schick (New York, M. Dekker, 1967), and in McCutcheon's *Emulsifiers & Detergents* (1989 Annual, M. C. Publishing Co.), the disclosures of which are incorporated herein by reference.

Recently, interest in α-sulfofatty acid esters (also referred to hereinafter as "sulfofatty acids") has increased due to the superior cleaning properties of these surfactants in hard water. While other surfactants have similar detergency in soft water, as water hardness increases α-sulfofatty acid esters exhibit increased cleaning performance as compared with other anionic surfactants. Thus, α-sulfofatty acid esters are an effective anionic surfactant that can be used in a wide variety of washing conditions.

α-Sulfofatty acid esters are typically manufactured as salts (i.e., a mixture of salt forms, typically mono- and di-salts). Di-salts result from hydrolysis of α-sulfofatty acid ester during manufacture, storage and in detergent compositions. In particular, mono-salts of α-sulfofatty acid ester hydrolyze in the presence of moisture and alkali-containing detergent components to form di-salts. For example, in formulations containing methyl ester sulfonate ("MES") that is well mixed with high pH components under aqueous conditions, the MES will hydrolyze nearly completely to the di-salt form. Such high pH components can include builders, such as silicates or carbonates, and bases. This chemical instability discourages the use of such anionic surfactants in many applications.

α-Sulfofatty acid esters are typically made from natural fats or oils. These fats and oils are usually free fatty acids or glycerol esters (i.e., mono-, di- or triglycerides). Free fatty acids are formed from glycerol esters by hydrolysis. The resulting fatty acids typically contain an even number of carbon atoms. These fatty acids are then esterified to form fatty acid esters. The esters are then sulfonated to form α-sulfofatty acid esters.

The surface active agent properties of α-sulfofatty acid esters are related to the chain lengths of the fatty acid portion of the molecules. For example, shorter chain length molecules (e.g., $C_8$-$C_{12}$ α-sulfofatty acid esters) are typically more water-soluble, but exhibit lesser surface active agent properties. Longer chain length (e.g., $C_{14}$-$C_{16}$) α-sulfofatty acid esters exhibit greater surface active agent properties, but are less water-soluble. Because α-sulfofatty acid esters are usually manufactured from natural sources, they are a mixture of different chain lengths. The properties of such mixtures are determined by the chain length distribution of the source of the fatty acids. Thus, α-sulfofatty acid esters from palm kernel (stearin) oil have different surfactant properties than α-sulfofatty acid esters from tallow. To overcome the limitations of single sources, blends of α-sulfofatty acid esters from multiple sources are prepared. Such blends are also limited, however, by the chain length distributions of each fatty acid source. For example, combining α-sulfofatty acid esters from palm kernel (stearin) oil ($C_6$-$C_{20}$ fatty acids) with α-sulfofatty acid esters from tallow ($C_{14}$-$C_{18}$ fatty acids) creates a mixture that has the average characteristics of the α-sulfofatty acid esters contained therein.

It has not been previously appreciated that the properties of α-sulfofatty acid ester mixtures can be improved by enriching such mixtures with particular chain length α-sulfofatty acid esters. Such enrichment allows certain beneficial properties (associated with particular chain length α-sulfofatty acid ester) to be enhanced without diluting such mixtures with other α-sulfofatty acid ester chain lengths.

SUMMARY OF THE INVENTION

The present invention provides compositions and processes for enriching mixtures of α-sulfofatty acid esters for particular chain lengths. By increasing the proportion of particular chain length α-sulfofatty acid esters, compositions are prepared that exhibit improved cleaning performance as well as improved aqueous solubility and reduced phase separation of the α-sulfofatty acid esters from other aqueous components.

The present invention includes compositions that are enriched for particular chain length α-sulfofatty acid ester(s). In one embodiment, a mixture of α-sulfofatty acid esters is enriched for a particular chain length α-sulfofatty acid ester. In another embodiment, a mixture of α-sulfofatty acid esters is enriched for a range of α-sulfofatty acid ester chain lengths. Such mixtures are enriched for a narrow range of such sulfofatty acid chain lengths or for multiple discrete chain lengths. Detergent components can also be added to the enriched mixture of α-sulfofatty acid esters. Suitable detergent components include builders, other anionic surfactants, nonionic surfactants, cationic surfactants, zwitterionic surfactants, polymer dispersants, oxidizing agents, biocidal agents, foam regulators, binders, anticaking agents, activators, catalysts, thickeners, stabilizers, UV protectors, fragrances, soil suspending agents, fillers, brighteners, enzymes, salts, inert ingredients, and the like.

Processes for enriching mixtures of α-sulfofatty acid esters are also provided. In one embodiment, a mixture of α-sulfofatty acid esters is enriched for one or more α-sulfofatty acid esters of particular chain lengths. For example, α-sulfofatty acid esters prepared from cohune oil, palm kernel oil or coconut oil are enriched for $C_{16}$ α-sulfofatty acid ester. In another embodiment, a mixture of α-sulfofatty acid esters is enriched for a narrow range of α-sulfofatty acid ester chain lengths. The α-sulfofatty acid ester mixture is enriched, for example, by supplementing the fatty acid feedstock with particular chain length fatty acid(s), by enriching for particular chain length fatty acid alkyl ester(s) prior to sulfonation, and/or by the addition of particular chain length α-sulfofatty acid esters to a mixture of such α-sulfofatty acids.

DETAILED DESCRIPTION OF THE INVENTION

The following description provides specific details, such as materials and dimensions, to provide a thorough understanding of the present invention. The skilled artisan, however, will appreciate that the present invention may be practiced without employing these specific details. Indeed, the present invention can be practiced in conjunction with processing, manufacturing or fabricating techniques conventionally used in the detergent industry. Moreover, the processes below describe only steps, rather than a complete process flow, for manufacturing the inventive compositions, and detergents containing the invented compositions.

A preferred embodiment is directed to compositions comprising enriched mixtures of α-sulfofatty acid esters. The mixture of α-sulfofatty acid esters include linear esters of $C_6$ to $C_{20}$ α-sulfofatty acid esters. The α-sulfofatty acid esters are typically of the following formula (I):

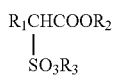

(I)

where $R_1$ is an unsubstituted or substituted alkyl group, $R_2$ is an unsubstituted or substituted alkyl group, and $R_3$ is hydrogen, a halogen, a metal, a monovalent or divalent cation, or an unsubstituted or substituted ammonium cation, such as monoethanolamine, diethanolamine, or triethanolamine. $R_1$ can be a $C_4$ to $C_{24}$ alkyl group including a $C_{10}$, $C_{12}$, $C_{14}$, and $C_{16}$ alkyl group. $R_2$ can be a $C_1$ to $C_8$ alkyl group, including a methyl group. $R_3$ can be a metal, including a cation that forms a water soluble salt with the α-sulfofatty acid ester, such as sodium, potassium or lithium.

More typically, the α-sulfofatty acid ester is of the following formula (II):

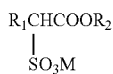

(II)

wherein $R_1$ is an alkyl group, $R_2$ is an alkyl group, and M is a monovalent metal. Typically, $R_1$ is an alkyl group containing 4 to 24 carbon atoms, such as a $C_{10}$, $C_{12}$, $C_{14}$, and $C_{16}$ alkyl group. $R_2$ is typically a $C_1$ to $C_4$ alkyl group, and is more typically a methyl group. M is typically an alkali metal, such as sodium.

The mixture of α-sulfofatty acid esters is prepared according to the desired properties of the final composition. Each α-sulfofatty acid ester is typically at least 50 weight percent mono-salt, preferably at least about 70 weight percent mono-salt. Methods of manufacturing α-sulfofatty acid esters are known to the skilled artisan. (See, e.g., U.S. Pat. Nos. 5,587, 500; 5,329,030; 5,382,677; 5,384,422; 4,671,900; 4,816,188; and The Journal of American Oil Chemists Society 52:323-29 (1975); the disclosures of which are incorporated herein by reference.) The mixture of α-sulfofatty acid esters can be manufactured according to any of these methods. α-Sulfofatty acid esters can be prepared from a variety of sources, including beef tallow, palm kernel oil, palm oil, peanut oil, coconut oil, soybean oil, canola oil, caster oil, cohune oil, coco butter, palm oil, white grease, cottonseed oil, corn oil, linseed oil, rape seed oil, yellow grease, tall oil, butter, lard, and mixtures thereof.

Other sources of fatty acids to make α-sulfofatty acid esters include caprylic ($C_8$), capric ($C_{10}$), lauric ($C_{12}$), myristic ($C_{14}$), myristoleic ($C_{14}$), palmitic ($C_{16}$), palmitoleic ($C_{16}$), stearic ($C_{18}$), oleic ($C_{18}$), linoleic ($C_{18}$), linolenic ($C_{18}$), ricinoleic ($C_{18}$), arachidic ($C_{20}$), gadolic ($C_{20}$), behenic ($C_{22}$) and erucic ($C_{22}$) fatty acids. α-Sulfofatty acid esters made from these sources are also within the scope of the present invention.

In one embodiment, the mixture of α-sulfofatty acid esters is a "broad cut." As used herein, the term "broad cut" refers to a mixture comprising at least 1% of $C_{10}$, $C_{12}$, $C_{14}$, $C_{16}$ and $C_{18}$ α-sulfofatty acid esters. Suitable sources of fatty acids that contain such a broad cut include palm kernel oil, coconut oil and cohune oil. In another embodiment, the mixture of α-sulfofatty acid esters is a "narrow cut," such as a mixture of $C_{12}$ and $C_{14}$ α-sulfofatty acid esters, a mixture of $C_{16}$ and $C_{18}$ α-sulfofatty acid esters, and the like. In another embodiment, different chain length α-sulfofatty acid esters are combined to form a mixture. For example, $C_{16}$ and $C_{18}$ sulfofatty acids (e.g., from tallow and/or palm stearin) generally provide better surface active agent properties, but can be less soluble. $C_8$-$C_{14}$ sulfofatty acids (e.g., from palm kernel and/or coconut) are more soluble in water, but have lesser surface active agent properties. Thus, suitable mixtures of α-sulfofatty acid esters include, for example, about 1 to about 100 weight percent of $C_8$, $C_{10}$, $C_{12}$, $C_{14}$, $C_{16}$ and $C_{18}$ α-sulfofatty acid esters. Other mixtures of α-sulfofatty acid esters are also within the scope of the present invention, as will be appreciated by the skilled artisan.

The mixture of α-sulfofatty acid esters is enriched for one or more chain length α-sulfofatty acid esters. As used herein, the term "enriched" means that the proportion of one or more chain length α-sulfofatty acid esters is increased relative to the proportion normally found in the α-sulfofatty acid ester mixture. For example, α-sulfofatty acid esters prepared from palm kernel oil and coconut oil typically comprise about 8.7 and 9 percent $C_{16}$ α-sulfofatty acid esters. Such mixtures can be enriched by adding additional $C_{16}$ α-sulfofatty acid esters. The resulting enriched mixture exhibits superior cleaning performance, good solubility and reduced phase separation. In another embodiment, the mixture of α-sulfofatty acid esters is enriched with a narrow range of α-sulfofatty acid esters. For example, α-sulfofatty acid esters prepared from palm kernel oil or cohune oil are typically a mixture of $C_6$-$C_{18}$ chain lengths. α-Sulfofatty acid esters derived from beef tallow are predominately $C_{16}$-$C_{18}$ α-sulfofatty acids. A narrow range fraction of α-sulfofatty acid esters from tallow can comprise about 96 percent $C_{16}$, about 3% $C_{14}$ and about 1% $C_{18}$ α-sulfofatty acid esters. Thus, α-sulfofatty acid esters prepared from palm kernel oil or cohune oil are enriched with the narrow range (e.g., $C_{16}$) fraction from tallow to form an enriched mixture of α-sulfofatty acid esters. In another embodiment, the narrow range comprises less than about 10%, more typically less than about 5%, of α-sulfofatty acid esters other than the predominant (e.g., $C_{16}$) α-sulfofatty acid ester. In still another embodiment, a mixture of shorter chain length α-sulfofatty acid esters (e.g., $C_{10}$, $C_{12}$ and $C_{14}$) is enriched with longer chain length α-sulfofatty acid(s) (e.g., $C_{16}$ and/or $C_{18}$) to form an enriched mixture.

The mixture of α-sulfofatty acid esters can be enriched by adding particular chain length α-sulfofatty acid ester(s) to that mixture. A mixture of α-sulfofatty acid esters can also be enriched by selectively removing non-preferred chain length α-sulfofatty acid esters from that mixture. The amount of enrichment can be chosen according to the desired properties of the final enriched mixture. For example, suitable proportions of enriched chain lengths to non-enriched chain lengths will include, but are not limited to, about 25 to about 50 weight percent enriched chain length to about 75 to about 50 weight percent non-enriched chain lengths. In another embodiment, the ratio of enriched to non-enriched chain lengths can range from greater than about 0.5:1, typically about 1:1 or about 2:1, and up to about 5:1 or about 6:1.

In some embodiments, the enriched mixture of α-sulfofatty acid esters is part of a detergent composition. Such detergent compositions preferably contain an effective amount of the α-sulfofatty acid ester mixture (i.e., an amount which exhibits the desired cleaning and surfactant properties). Typically, the detergent composition contains at least about 5 weight percent of the enriched α-sulfofatty acid ester mixture. More typically, the detergent composition contains at least about 15 weight percent of the enriched α-sulfofatty acid ester mixture. In another embodiment, the detergent composition contains at least about 30 weight percent, and/or at least about 35 weight percent, of the enriched α-sulfofatty acid ester mixture.

Suitable detergent components that can be combined with the enriched α-sulfofatty acid ester mixture include builders, other anionic surfactants, nonionic surfactants, cationic surfactants, zwitterionic surfactants, polymer dispersants, oxidizing agents, biocidal agents, foam regulators, binders, anticaking agents, activators, catalysts, thickeners, stabilizers, UV protectors, fragrances, soil suspending agents, fillers, brighteners, enzymes, salts, inert ingredients, and the like.

Suitable non-ionic surfactants include those containing an organic hydrophobic group and a hydrophilic group that is a reaction product of a solubilizing group (such as a carboxylate, hydroxyl, amido or amino group) with an alkylating agent, such as ethylene oxide, propylene oxide, or a polyhydration product thereof (such as polyethylene glycol). Such nonionic surfactants include, for example, polyoxyalkylene alkyl ethers, polyoxyalkylene alkylphenyl ethers, polyoxyalkylene sorbitan fatty acid esters, polyoxyalkylene sorbitol fatty acid esters, polyalkylene glycol fatty acid esters, alkyl polyalkylene glycol fatty acid esters, polyoxyethylene polyoxypropylene alkyl ethers, polyoxyalkylene castor oils, polyoxyalkylene alkylamines, glycerol fatty acid esters, alkylglucosamides, alkylglucosides, alkylamine oxides, and alkanolamides. Other suitable surfactants include those disclosed in U.S. Pat. Nos. 5,133,892 and 6,034,045, the disclosures of which are incorporated herein by reference. In one embodiment, the composition is substantially free of nonylphenol nonionic surfactants. In this context, the term "substantially free" means less than about 1 weight percent nonylphenol nonionic surfactant.

Suitable builders include silicated salts. The term "silicated salt" means a non-phosphate salt, such as a carbonate, sulfate, alkali metal carbonate, alkali metal sulfate, ammonium carbonate, bicarbonate, sesquicarbonate, or mixtures thereof, that has been treated with a silicate salt. Silicated salts and methods for preparing such salts are disclosed in U.S. Pat. No. 4,973,419, the disclosure of which is incorporated herein by reference.

Suitable silicate builders include non-phosphate silicate salts, such as polysilicates and alkali metal silicates. One preferred alkali metal silicate is a sodium silicate, such as a hydrous sodium silicate having an $SiO_2$ to $Na_2O$ ratio ranging from about 2.0 to about 2.4. Suitable alkali metal silicates further include those sold by PQ Corporation under the trade names BRITESIL® H20, BRITESIL® H24 and BRITESIL C-24. Other suitable silicate builders include wholly or partially crystallite layer-form silicates of the formula $Na_2Si_x.O_{2x+1}yH_2O$, where x ranges from about 1.9 to about 4 and y ranges from 0 to about 20. Such silicates are described, for example, in U.S. Pat. No. 5,900,399, the disclosure of which is incorporated herein by reference.

Other suitable silicate builders include phyllosilicates or disilicates, such as those having the formula $Na_2O.2SiO_2$ or $Na_2Si_2O_5.yH_2O$, where y is an integer. Preferred disilicates include β-sodium disilicates, such as those described in International Patent Application WO-A-91-08171, the disclosure of which is incorporated herein by reference. Disilicates sold under the trade names SKS® 6 and SKS® 7 by Hoescht AG and Clariant Corporation can also be used.

Other suitable builders include phosphate and aluminosilicate builders. The term "phosphate builders" means both inorganic and organic phosphate-containing builders such as alkali metal phosphates, orthophosphates, polyphosphates, tripolyphosphates, pyrophosphates, and polymeric phosphates. Aluminosilicate builders include those known in the art, such as those of the formulae (III) and (IV):

$$Na_z[(AlO_2)_z(SiO_2)_y].xH_2O \qquad (III)$$

where z and y are integers greater than 5, x is an integer ranging from 15 to 264, and the molar ratio of z to y ranges from about 1.0 to about 0.5; and

$$M_z(zAlO_2.ySiO_2) \qquad (IV)$$

where M is sodium, potassium, ammonium, or substituted ammonium, z ranges from about 0.5 to about 2, and y is 1. Examples of such aluminosilicate builders include zeolite NaA, zeolite NaX, zeolite P, zeolite Y, hydrated zeolite 4A, zeolite MAP or mixtures thereof.

Suitable polymer dispersants include polymers and co-polymers of acrylic acid, methacrylic acid, maleic acid, fumaric acid, itaconic acid, and water-soluble salts thereof, such as alkali metal, ammonium, or substituted ammonium salts. Suitable polymer dispersants further include those sold under the trade names ACUSOL® 445 (polyacrylic acid), ACUSOL® 445N (the sodium salt of polyacrylic acid), ACU-SOL® 460N (a maleic acid/olefin copolymer sodium salt), and ACUSOL® 820 (acrylic copolymer), all sold by Rohm and Haas.

Other anionic surfactants include alkylbenzenesulfonates, alkyl or alkenyl ether sulfates, alkyl or alkenyl sulfates, olefin sulfonates, alkyl or alkenyl ether carboxylates, amino acid-type surfactants, and N-acyl amino acid-type surfactants. In another embodiment, the composition is substantially free of other anionic surfactants.

Suitable oxidizing agents include chlorine and non-chlorine-containing oxidizing agents. Suitable non-chlorine oxidizing agents include oxygen bleaches, such as perborates, percarbonates, persulfates, dipersulfates, sodium carbonate peroxyhydrate, sodium pyrophosphate peroxyhydrate, urea peroxyhydrate, and sodium peroxide. Other suitable non-chlorine oxidizing agents include bleach activators, such as tetraacetyl ethylene diamine (TAED), sodium benzoyl oxybenzene sulfonate, choline sulfophenyl carbonate, and those described in U.S. Pat. Nos. 4,915,854 and 4,412,934, the disclosures of which are incorporated herein by reference. Other suitable non-chlorine oxidizing agents include a catalyst such as manganese or other transition metals in combination with such oxygen bleaches.

Other suitable oxidizing agents include percarboxylic acid bleaching agents and salts thereof, such as magnesium monoperoxyphthalate hexahydrate and the magnesium salts of meta-chloro perbenzoic acid, 4-nonylamino-4-oxoperoxybutyric acid and diperoxydodecanedioic acid. Other oxidizing agents include those described in U.S. Pat. Nos. 4,483,781, 4,634,551, and 4,412,934, as well as European Patent Application No. 0,133,354, the disclosures of which are incorporated herein by reference.

Suitable oxidizing agents include non-oxygen-containing agents, such as photoactivated bleaching agents. Suitable photoactivated bleaching agents include sulfonated zinc and metal phthalocyanines, such as aluminum and zinc phthalocyanines. Other suitable photoactivated bleaching agents are described in U.S. Pat. No. 4,033,718, the disclosure of which is incorporated herein by reference.

Chlorine-containing agents include organic and/or inorganic compounds capable of having their chlorine liberated in the form of active chlorine on dissolution in water. Typical examples of such chlorine-containing agents include hypochlorites such as alkali metal (calcium and lithium) hypochlorites; chlorinated trisodium phosphate; chlorinated sulfonamides; halogenated hydantoins, such as 1,3-dichloro-5,5-dimethylhydantoin; polychlorocyanurates (usually containing alkali metals such as sodium or potassium salts); chlorine-substituted isocyanuric acid; alkali-metal salts of isocyanuric acid, such as potassium or sodium dihydrate; and other anhydrous chlorine-containing agents known in the detergent industry.

Suitable biocidal agents include TAED, TAED combined with a persalt, triclosan (5-chloro-2(2,4-dichloro-phenoxy) phenol)), and quaternary ammonium compounds such as alkyl dimethyl ammonium chlorides, alkyl trimethyl ammonium chlorides, dialkyl dimethyl ammonium chlorides, benzalkonium chloride, parachlorometaxylene and alkyl dimethyl benzyl ammonium chloride. Other biocidal agents include those sold under the trade names BARDAC® and BARQUAT® by the Lonza Group and those sold under the trade name BTC by the Stepan Company.

Suitable optical brighteners include stilbenes such as TINOPAL® AMS, distyrylbiphenyl derivatives such as TINOPAL® CBS-X, stilbene/naphthotriazole blends such as TINOPAL® RA-16, all sold by Ciba Geigy, oxazole derivatives and coumarin brighteners.

Suitable enzymes include any of those known in the art, such as amylolytic, proteolytic or lipolytic type, and those listed in U.S. Pat. No. 5,324,649, the disclosure of which is incorporated herein by reference. One preferred protease, sold under the trademark SAVINASE® by NOVO Industries A/S, is a subtillase from *Bacillus lentus*. Other suitable enzymes include amylases, lipases, and cellulases, such as ALCALASE® (bacterial protease), EVERLASE® (protein-engineered variant of SAVINASE®), ESPERASE® (bacterial protease), LIPOLASE® (fungal lipase), LIPOLASE ULTRA (Protein-engineered variant of LIPOLASE), LIPOPRIME™ (protein-engineered variant of LIPOLASE), TERMAMYL® (bacterial amylase), BAN (Bacterial Amylase Novo), CELLUZYME® (fungal enzyme), and CAREZYME® (monocomponent cellulase), sold by Novo Industries A/S.

Compositions according to the present invention can be prepared by any suitable process or combination of processes that yield the desired composition, according to the present invention. The enriched mixture of α-sulfofatty acid esters is typically prepared by one of a variety of methods. In one embodiment, the enriched mixture of α-sulfofatty acid esters is prepared by combining particular chain length fatty acid(s) with a mixture of fatty acids of differing chain lengths. The enriched fatty acid mixture is then esterified and sulfonated to form the enriched mixture of α-sulfofatty acid esters. In another embodiment, the enriched mixture is prepared by combining particular chain length fatty acid ester(s) with a mixture of fatty acid esters of differing chain lengths. The enriched mixture of fatty acid esters is then sulfonated to form the enriched mixture of α-sulfofatty acid esters. In yet another embodiment, the enriched mixture of α-sulfofatty acid esters is prepared by combining particular chain length α-sulfofatty acid ester(s) with a mixture of α-sulfofatty acid esters of differing chain lengths.

In a preferred embodiment, the enriched mixture of α-sulfofatty acid esters are prepared by combining $C_{16}$-enriched fatty acids, $C_{16}$-enriched fatty acid alkyl esters, or $C_{16}$-enriched α-sulfofatty acid esters with a mixture of fatty acids, fatty acid alkyl esters or α-sulfofatty acid esters, respectively. These mixtures are esterified and sulfonated, as necessary, to form an enriched mixture of α-sulfofatty acid esters. The proportions of carbon chain lengths in the mixture are selected according to the desired surfactant properties of the final composition.

One method of preparing an enriched mixture of α-sulfofatty acid esters is to provide a natural fat or oil that includes the preferred chain length fatty acids, and then fractionating the fatty acids to enrich for those preferred chain lengths. Typically, such a natural fat or oil has a significant concentration (at least about 25 percent and preferably about 35 percent) of the preferred chain length fatty acids. For example, a suitable fatty acid source, such as palm stearin oil or tallow, is provided and fed to a separation apparatus, such as a fractionation tower or liquid-liquid extraction. (See, e.g., *Perry's Chemical Engineers' Handbook* ($6^{th}$ Ed.), chapter 15 (1984), the disclosure of which is incorporated herein by reference). The $C_{16}$-enriched stream exiting the separation apparatus is then combined with a mixture of fatty acids. The enriched mixture of fatty acids is then esterified to make an enriched mixture of fatty acid alkyl esters, which is then sulfonated to form the enriched mixture of α-sulfofatty acid esters. The other stream(s) exiting the separation apparatus can be used in any desired manner. For example, when palm stearin oil is fractionated, the stream containing mostly $C_{16}$ fatty acids is used to make the α-sulfofatty acid esters while the stream containing mostly $C_{18}$ fatty acids is used in the process of making an alkanolamide or a polyalkoxylated alkanolamide.

Another method is to prepare fatty acid alkyl esters comprising the preferred fatty acid alkyl esters, such as fatty acid methyl esters, and then fractionating the fatty acid alkyl esters to enrich for preferred chain length fatty acid alkyl esters. Preferably, such fatty acid alkyl esters have a significant concentration (at least about 25 percent and preferably about 35 percent) of the desired fatty acid alkyl esters. For example, a suitable fatty acid alkyl ester source, such as esterified tallow, is provided and fed to a separation apparatus, such as a fractionation tower or liquid-liquid extraction. (See, e.g., *Perry's Chemical Engineers' Handbook* ($6^{th}$ Ed.), chapter 15 (1984), the disclosure of which is incorporated herein by reference.) The $C_{16}$-enriched stream exiting the separation apparatus is then used to make $C_{16}$-enriched α-sulfofatty acid esters. The other stream(s) exiting the separation apparatus can be used in any desired manner, such as to make alkanolamides or polyalkoxylated alkanolamides.

The enriched α-sulfofatty acid ester mixture can also be prepared by combining a mixture of α-sulfofatty acid esters with the desired chain length α-sulfofatty acid ester(s) to enrich the mixture. For example, a broad cut mixture of α-sulfofatty acid esters from cohune oil, palm kernel oil or coconut oil can be mixed with a narrow range of $C_{16}$ (e.g., $C_{14}$-$C_{16}$-$C_{18}$) α-sulfofatty acid esters.

Any suitable mixing apparatus can be used to combine the fatty acids, fatty acid alkyl esters or α-sulfofatty acid esters. (See, e.g., *Perry's Chemical Engineers' Handbook* (6$^{th}$ Ed.), chapters 19 and 21 (1984), the disclosure of which is incorporated herein by reference.) In some embodiments, the amounts of different chain lengths can be combined in any suitable ratios. For example, when a first source of fatty acids is palm kernel oil (PKO) and a second source of fatty acids is $C_{16}$-fatty acids from palm stearin oil (PSO), these two sources are mixed in amounts of about 40-60 weight percent PKO with about 60-40 weight percent $C_{16}$-enriched PSO, and preferably about 50-55 weight percent PKO with about 50-45 weight percent $C_{16}$-enriched PSO. The fatty acids are then esterified to form fatty acid alkyl esters, which are then sulfonated.

In another example, when a first source of fatty acid alkyl esters is esterified palm kernel oil (ePKO) and a second source of fatty acid alkyl esters is esterified, $C_{16}$-enriched palm stearin oil (ePSO), these two sources are mixed in amounts of about 40-60 weight percent ePKO with about 60-40 weight percent $C_{16}$-enriched ePSO, and preferably about 50-55 weight percent ePKO with about 50-45 weight percent $C_{16}$-enriched ePSO. The enriched mixture of fatty acid alkyl esters is then sulfonated to form the enriched mixture of α-sulfofatty acid esters.

The sulfonation process can be performed according to any sulfonation process as known in the art, such as the processes described in U.S. Pat. Nos. 5,587,500; 5,329,030; 5,382,677; 5,384,422; 4,671,900; 4,816,188; and The Journal of American Oil Chemists Society 52:323-29 (1975), the disclosures of which are incorporated herein by reference. Other sulfonation processes known in the art include those processes using both hydrogen peroxide and a halogen bleach in a two step bleaching operation; processes that use ultra purified fatty acid alkyl ester feedstocks along with a single step hydrogen peroxide neutral bleaching process; and re-esterification processes using only hydrogen peroxide acidic bleaching with typical quality fatty acid alkyl ester feedstocks.

The α-sulfofatty acid ester (e.g., a methyl ester sulfonate) is typically prepared by feeding the fatty acid alkyl ester feedstock and $SO_3$ gas to a suitable reactor, such as a falling film reactor. Any source of $SO_3$ gas can be used. For example, to generate $SO_3$ gas, dry air is compressed, cooled, dried and then mixed with liquid sulfur, supplied from a suitable reservoir, to make sulfur dioxide. The sulfur can be uniformly combusted, for example, by using a sulfur burner to control the molar ratio of air to sulfur. The sulfur dioxide is cooled, such as in a double-pipe cooler, prior to being delivered to a catalytic converter where the sulfur dioxide gas is filtered and converted to the sulfur trioxide gas.

In the sulfonation reaction, or sulfonator, the molar ratio of the methyl ester feed to the $SO_3$ gas is optimized for sulfonation of the fatty acid alkyl ester feedstock. The step of sulfonation is typically the rapid reaction of the fatty acid alkyl ester with two molecules of $SO_3$ to form an adduct. The second step of the sulfonation reaction, which is usually slower and requires longer time and elevated temperatures, is rearrangement of the adduct to form a fatty acid alkyl ester sulfonic acid, releasing the second molecule of $SO_3$, which then reacts with another fatty acid alkyl ester molecule. The sulfur dioxide gas that is generated in the two-step process can then be removed and can be recycled.

The fatty acid alkyl ester sulfonic acid can optionally be bleached. Because the elevated temperatures in the sulfonation process darken the acid, a bleaching step may be required to lighten the acid to acceptable levels. An advantageous fatty acid alkyl ester sulfonic acid feedstock used in the manufacturing process is a natural oil derivative that has low acid values, a narrow molecular weight distribution, contains little or no paraffinic compounds, and has been hydrogenated to reduce the iodine content, thereby reducing the presence of double bonds that cause the dark color when sulfonated. The bleaching process can be carried out in two stages. First, the fatty acid alkyl ester sulfonic acid is reacted with less than about 5 weight percent alkanol, such as methanol, to produce the desired mono-salt and to inhibit formation of the di-salt to less than about 30%. Second, hydrogen peroxide is reacted with the fatty acid alkyl ester sulfonic acid to reduce the color. The order of the two bleaching steps can be changed, as desired. The fatty acid alkyl ester sulfonic acid is typically degassed in an inert gas blanketed flash feed tank to remove oxygen and low molecular compounds.

The fatty acid alkyl ester sulfonic acid is then neutralized to form α-sulfofatty acid ester. The fatty acid alkyl ester sulfonic acid is neutralized with any suitable base that will yield the desired salt. Typically, sodium hydroxide (NaOH) is reacted with fatty acid alkyl ester sulfonic acid to produce sodium α-sulfofatty acid ester.

Finally, the α-sulfofatty acid ester is dried. The product leaving the neutralizer typically contains about 65-70% solids and 10-15% methanol. The α-sulfofatty acid ester is heated to an elevated temperature and fed to a dryer, preferably a steam-heated vacuum flash dryer, to strip the methanol and water (and other volatile components). The resulting product contains about 2-4% water. This product can optionally be cooled.

In another embodiment, the α-sulfofatty acid ester is optionally partially or fully coated to protect the α-sulfofatty acid ester from moisture and/or minor amount of additional di-salt formation. Such a coating can prevent the contact of bases, moisture, and other di-salt causing substances with the sulfofatty acid. Such a coating can be water-resistant. In such an embodiment, the coating typically has a melting point within normal washing temperatures. The coating can also be water-soluble.

Suitable coatings include, for example, polyvinyl alcohol, partially or fully hydrolyzed polyvinyl alcohol, polyvinyl acetate, polyvinyl pyrrolidone, polyvinyl-methylmethacrylate copolymer, maleic acid/acrylic acid copolymer, ethylene/maleic anhydride copolymer, polyethylene glycol, acrylic acid polymer, carboxymethyl cellulose, cellulose ether, paraffin waxes, fatty acids, methyl ester sulfonate, soaps, waxes, water-soluble polymers, water-swellable polymers, or copolymers, salts or mixtures of any of these.

The coating can be applied to the α-sulfofatty acid ester according to techniques conventionally used in the detergent industry. Other techniques for applying coatings, such as those used in the pharmaceutical industry, are also within the scope of the present invention, as will be appreciated by the skilled artisan. Examples of suitable techniques for applying a coating include dip coating, spin coating, spray coating, spray drying (including spray drying using counter-current or co-current techniques), agglomeration and fluid bed drying. Suitable fluid bed dryers include, for example, static, vibrating, high-shear granulating, vacuum fluid bed, tablet pan coating, rotor processing and high speed fluid bed dryers. Following coating at least a portion of the α-sulfofatty acid ester, the coating can be dried, as necessary, to remove excess moisture or other liquid.

In another embodiment, the enriched mixture of α-sulfofatty acid esters is combined with other detergent components in any suitable mixing apparatus. Suitable apparatuses include dry blenders, agglomerators, spray drying equipment, fluid bed mixers, or any solid-solid, liquid-solid, or liquid-liquid mixing apparatus known in the art. (See, e.g., *Perry's Chemical Engineers' Handbook* (6$^{th}$ Ed.), chapter 19 (1984).) Water and/or solvents can be added to aid in this mixing process. Further, on exiting the mixing apparatus, the composition is optionally dried and combined with other detergent components as known in the art.

Other embodiments of the present invention are exemplified in the following examples, which illustrate embodiments of the present invention, although the invention is not intended to be limited by or to these examples.

Example 1

A $C_{16}$-enriched methyl ester sulfonate was prepared according to the following process. Palm kernel oil ("PKO") and palm stearin oil ("PSO") were separately esterified with an alkanol (e.g., methanol). The esterified palm stearin oil was then fractionated in a tower. The $C_{16}$ fraction of the palm stearin oil (predominately $C_{16}$'s with small amounts of $C_{14}$ and $C_{18}$ chain lengths) was then mixed with the esterified palm kernel oil in a ratio of about 1:1. The mixture was then sulfonated in a falling film reactor. The resulting fatty acid alkyl ester sulfonic acid was reacted with NaOH to obtain an enriched sodium α-sulfofatty acid ester.

Example 2

A detergent composition (i.e., one with $C_{16}$-enriched methyl ester sulfonate) is made according to the following process. First, palm kernel oil is esterified with an alkanol (e.g., methanol) to form a first fatty acid alkyl ester. Tallow is esterified with an alkanol (e.g., methanol) to form a second fatty acid alkyl ester. The second tallow fatty acid alkyl ester is then fractionated in a tower. The $C_{16}$-enriched fatty acid alkyl ester fraction is combined with the first fatty acid alkyl ester (from PKO) in a ratio of about 45-55 weight percent to 55-45 weight percent, respectively. The resulting mixture is then sulfonated in a falling film reactor and the resulting fatty acid alkyl ester sulfonic acid is reacted with NaOH to obtain a sodium α-sulfofatty acid ester. This sodium α-sulfofatty acid ester is then added to other detergent components to obtain a final detergent composition.

Example 3

A $C_{16}$-enriched methyl ester sulfonate is prepared according to the following process. Palm kernel oil is combined with a $C_{16}$-enriched fraction of fatty acids from tallow. The enriched mixture is then esterified with an alkanol and then sulfonated in a falling film reactor. The resulting fatty acid alkyl ester sulfonic acid is reacted with NaOH to obtain a sodium α-sulfofatty acid ester.

Having described in detail the present invention, the invention defined by the appended claims is not limited by particular details set forth in the above description, as many apparent variations thereof are possible without departing from the spirit or scope thereof.

We claim:

1. A detergent composition comprising a mixture of $C_{10}$, $C_{12}$, $C_{14}$, $C_{16}$ and $C_{18}$ methyl ester sulfonates, wherein said mixture comprises about 50 weight percent to about 75 weight percent of a first methyl ester sulfonate comprising $C_{10}$, $C_{12}$, $C_{14}$, $C_{16}$ and $C_{18}$ chain lengths prepared from a natural fat or oil, and about 50 weight percent to about 25 weight percent of a second methyl ester sulfonate comprising predominantly a $C_{16}$ or $C_{18}$ chain lengths, wherein said mixture has an increased proportion of $C_{16}$ or $C_{18}$ chain lengths relative to the normal proportion of $C_{16}$ or $C_{18}$ chain lengths found in said natural fat or oil.

2. The detergent composition of claim 1, wherein the mixture of $C_{10}$, $C_{12}$, $C_{14}$, $C_{16}$ and $C_{18}$ methyl ester sulfonates has an increased proportion of $C_{16}$ chain lengths relative to the normal proportion of $C_{16}$ chain lengths found in said natural fat or oil.

3. The detergent composition of claim 1, wherein the composition comprises at least about 25 weight percent of the second methyl ester sulfonate, based on the total weight percent of methyl ester sulfonates.

4. The detergent composition of claim 1, wherein the composition comprises at least about 35 weight percent of the second methyl ester sulfonate, based on the total weight percent of methyl ester sulfonates.

5. The detergent composition of claim 1, wherein the composition comprises about 50 weight percent of the second methyl ester sulfonate, based on the total weight percent of methyl ester sulfonates.

6. The detergent composition of claim 1, wherein the first methyl ester sulfonate is prepared from palm kernel oil, cohune oil or coconut oil, and the second methyl ester sulfonate is prepared from palm stearin oil or tallow.

7. The detergent composition of claim 1, wherein the second methyl ester sulfonate comprises predominantly $C_{16}$ chain lengths.

8. The detergent composition of claim 1, wherein the mixture comprises at least about 35 weight percent $C_{16}$ chain lengths.

9. The detergent composition of claim 1, wherein the mixture comprises at least about 50 weight percent $C_{16}$ chain lengths.

10. The detergent composition of claim 1, further comprising at least one additional component selected from the group consisting of a nonionic surfactant, a cationic surfactant, a secondary anionic surfactant, a zwitterionic surfactant, a polymer dispersant, an oxidizing agent, a biocidal agent, a foam regulator, a builder, a binder, an anticaking agent, an activator, a catalyst, a thickener, a stabilizer, a UV protector, a fragrance, a soil suspending agent, a filler, a brightener, an enzyme, a salt and an inert ingredient.

11. The detergent composition of claim 10, wherein said composition comprises a nonionic surfactant, a builder and an enzyme.

12. The detergent composition of claim 10, wherein said secondary anionic surfactant, if present in said composition, is present at less than about 1 weight percent.

* * * * *